US006402700B1

(12) United States Patent
Richards (10) Patent No.: US 6,402,700 B1
(45) Date of Patent: Jun. 11, 2002

(54) PAP SMEAR APPARATUS AND METHOD

(76) Inventor: Michael Owen Richards, P.O. Box 2320, Waldron, AR (US) 72958

( * ) Notice: Subject to any disclaimer, the term of this patent is extended or adjusted under 35 U.S.C. 154(b) by 0 days.

(21) Appl. No.: 09/721,026

(22) Filed: Nov. 21, 2000

Related U.S. Application Data (60) Provisional application No. 60/167,099, filed on Nov. 23, 1999.

(51) Int. Cl.7 ............................................... A61B 10/00
(52) U.S. Cl. ..................................................... 600/562
(58) Field of Search ............................... 600/562, 563, 600/564, 565, 566, 567, 568, 569, 570, 571, 572–583; 128/883, 884

(56) References Cited

U.S. PATENT DOCUMENTS

| | | | |
|---|---|---|---|
| 4,620,548 A | | 11/1986 | Hasselbrack |
| 4,628,941 A | | 12/1986 | Kosasky |
| 5,121,752 A | | 6/1992 | Camma |
| 5,605,161 A | * | 2/1997 | Cross ........................ 600/584 |
| 5,769,090 A | * | 6/1998 | Brown ........................ 128/883 |
| 5,795,289 A | * | 8/1998 | Wyttenbach ................. 600/207 |
| 6,096,047 A | * | 8/2000 | Smit ........................... 606/119 |
| 6,155,990 A | * | 12/2000 | Fournier ...................... 600/572 |

* cited by examiner

Primary Examiner—Kevin Shaver
Assistant Examiner—Pamela L Wingood
(74) Attorney, Agent, or Firm—Charlotte W. Catlett (57) ABSTRACT

A personal PAP smear apparatus and method for collecting a non-intrusive cell or tissue sample for medical testing such as cervical cancer screening is provided. The apparatus includes an insertion handle, a flexible speculum ring, and a means for movably attaching the speculum ring to the insertion handle. The speculum ring includes two adjacent ring halves circumferentially divided to permit expansion of the collapsed speculum tube housed within the hollow ring halves. The method of the invention includes insertion of the flexible speculum assembly into the user's vagina, movement of the speculum ring to a raised position encircling the user's cervix, separating the ring halves to expand the tube and define the speculum bore, and inserting a sampling tool through the bore until it touches the cervix or surrounding surface areas for tissue sampling.

20 Claims, 11 Drawing Sheets

PAP SMEAR APPARATUS AND METHOD

CROSS REFERENCE TO RELATED APPLICATIONS

This application is related to the provisional application Ser. No. 60/167,099, filed on Nov. 23, 1999, entitled Pap Smear Apparatus and Method.

STATEMENT REGARDING FEDERALLY SPONSORED RESEARCH OR DEVELOPMENT

Not Applicable.

BACKGROUND OF THE INVENTION

1. Field of the Invention

This invention relates to gynecological medical devices, and more particularly to a medical tool and method for enabling a woman to collect a personal cervical cell sample for use during a Papanicalou (PAP) test, commonly known as a PAP smear.

2. Description of Related Art Including Information Disclosed Under 37 CFR 1.97 and 1.98

The PAP smear is an important routine gynecological test usually done annually in sexually active females to screen for cervical cancer. The tests known in the art typically require an in office visit with a gynecologist where the doctor takes a sample of the cervix for lab analysis. Current medical practice requires a gynecologist to insert a speculum into the patient's vagina to access the cervix for tissue sample collection. Many women find this method an uncomfortable, intrusive exam, and opt to not have the routine screening performed.

While certain groups of women are recognized to be at a higher risk for cervical cancer and exposure to a variety of Human Papilloma Virus subtypes, many monogamous women do not fall into the high risk categories. For these women, the screening guidelines recommend testing every three years after two normal annual PAP smears. For many women, the routine screening test would be regularly performed if it could be done in a non-intrusive, private manner.

Of particular relevance to the instant invention is U.S. Pat. No. 5,121,752 to Canna. Canna '752 discloses a self-obtaining PAP smear apparatus which must be used by a woman in an upright position. The apparatus includes a rigid, cylindrical speculum, angled endocervical sampler and an elongated angled spatula. The cylindrical speculum includes an angled front orifice designed to fit about the cervix. After insertion, a mirror is used for visual observation to affirm correct placement of the orifice around the cervix. In actual practice, however, obtaining a clear view by speculum of the cervix is difficult even under direct vision. In addition, the length and rigidity of the speculum prevent the use of digital assistance to confirm proper placement.

Although the aforementioned reference discloses one method and apparatus for self-obtaining PAP smears, it fails to teach or disclose an efficient, easy to use method and apparatus that enables digital location of the cervix for accurate placement of the speculum and reliable sampling of the cervical tissue. The present invention meets these needs. The invention provides an efficient tool for privately performing a non-intrusive PAP smear without the need for assistance by a gynecologist or other medical practitioner.

BRIEF SUMMARY OF THE INVENTION

The present invention is a PAP smear apparatus and method of use for enabling a user to obtain a personal PAP smear. The apparatus of the invention includes a flexible speculum, an insertion handle, and a means for movably attaching the flexible speculum to the insertion handle. The flexible speculum includes a hollow ring housing a collapsed or compressed tube. The ring is split along its circumference defining two separate, adjacent halves. The tube is attached to the ring halves at its ends and includes a reinforcement mechanism to prevent the bore from collapsing when the tube is expanded during use.

In one embodiment, the tube's reinforcement mechanism is a coiled wire, which spirals circumferentially throughout the length of the tube.

In a preferred embodiment, the means for movably attaching the flexible speculum to the insertion handle is a ratchet mechanism wherein the ratchet catch is on the first ring half and the ratchet spur is proximal to the first end of the insertion handle.

In another aspect of the invention, a means for securing the first and second ring halves together until the user desires to expand the compressed tube is provided. In one aspect, the securing means is a latching mechanism such as a spring latch, hinge, or hook. In another aspect, the insertion handle holds the second ring half adjacent to the first ring half when the ring is in its horizontal insertion position.

It is another object of the invention to provide a method for enabling a user to obtain a cervical PAP smear without the aid of a gynecologist or other medical professional. The method includes the steps of inserting the flexible speculum into the user's vagina, positioning the speculum ring around the user's cervix and separating the ring halves. Separating the ring halves enables expansion of the compressed tube housed within the ring by drawing the free half back through the user's vagina. After the tube is expanded, the user may insert a sampling tool through the bore of the tube to wipe the cervix, the endocervical canal and surrounding surface areas to collect a cell or tissue sample. Once the sampling is completed using one or more sampling tools, the flexible speculum is removed from the user's vagina and discarded.

BRIEF DESCRIPTION OF THE SEVERAL VIEWS OF THE DRAWINGS

The invention will be better understood and its numerous objects and advantages will become more apparent to those skilled in the art by reference to the following drawings, in conjunction with the accompanying specification, in which.

DESCRIPTION OF THE INVENTION

The present invention is a personal PAP smear apparatus and method for collecting a non-intrusive cell or tissue sample for medical testing such as cervical cancer screening. Referring to FIGS. 1–4 and 6–7 of the drawings, the apparatus of the invention 10 includes a speculum ring assembly 20 movably attached to an insertion handle 12. Insertion handle 12 includes a first end 14, a second end 16, and an optional ring holder 18 proximal to end 16.

Figure 1:
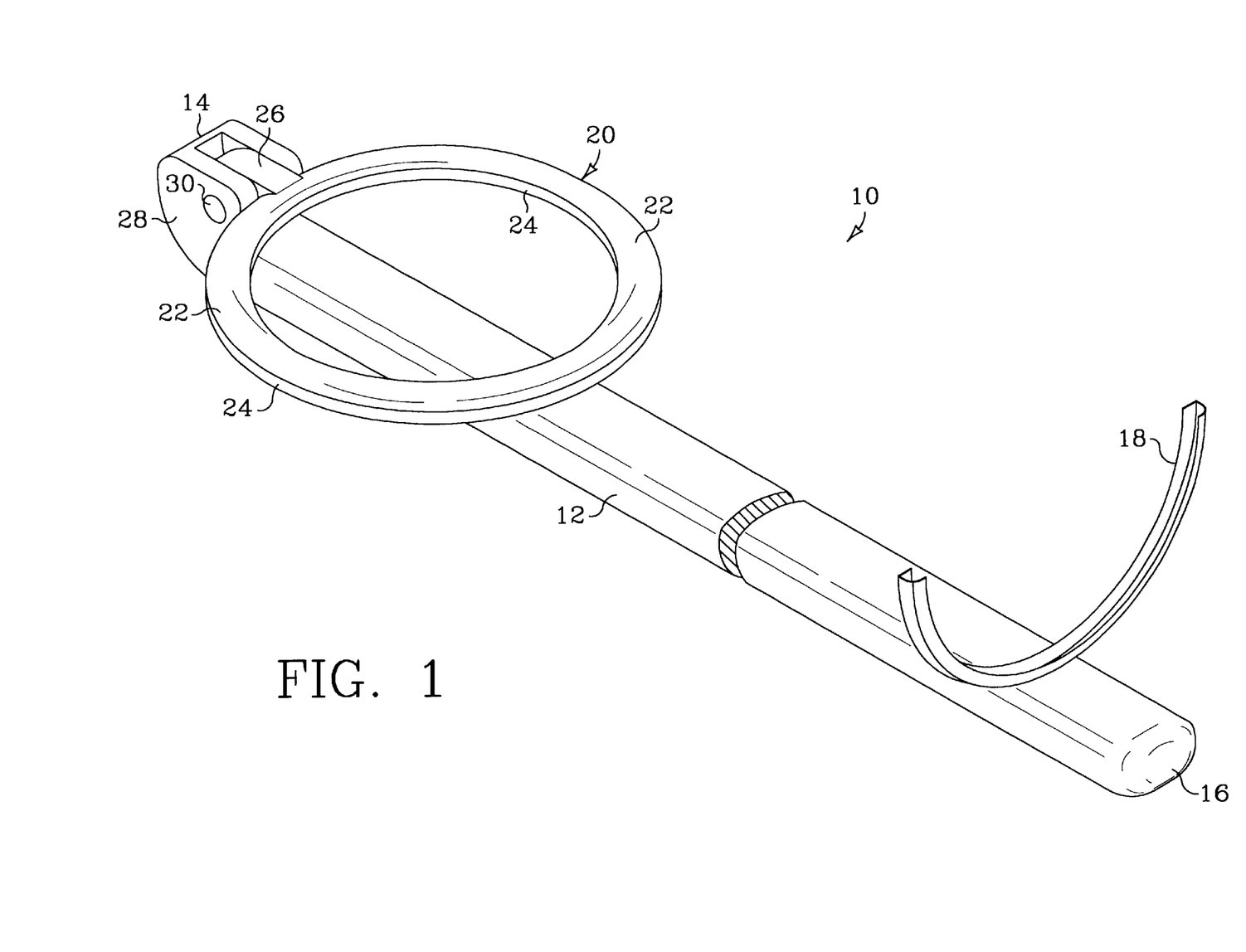
FIG. 1 is a perspective view of an embodiment of the PAP smear sampling apparatus depicting the speculum ring in the horizontal, compressed position.
Figure 2:
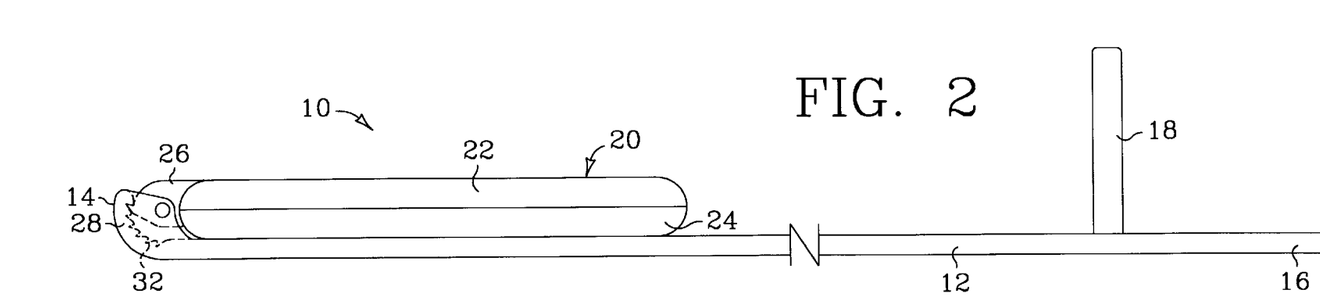
FIG. 2 is a side elevation view of the embodiment of the present invention shown in FIG. 1 depicting the speculum ring in the horizontal, compressed position.
Figure 3:
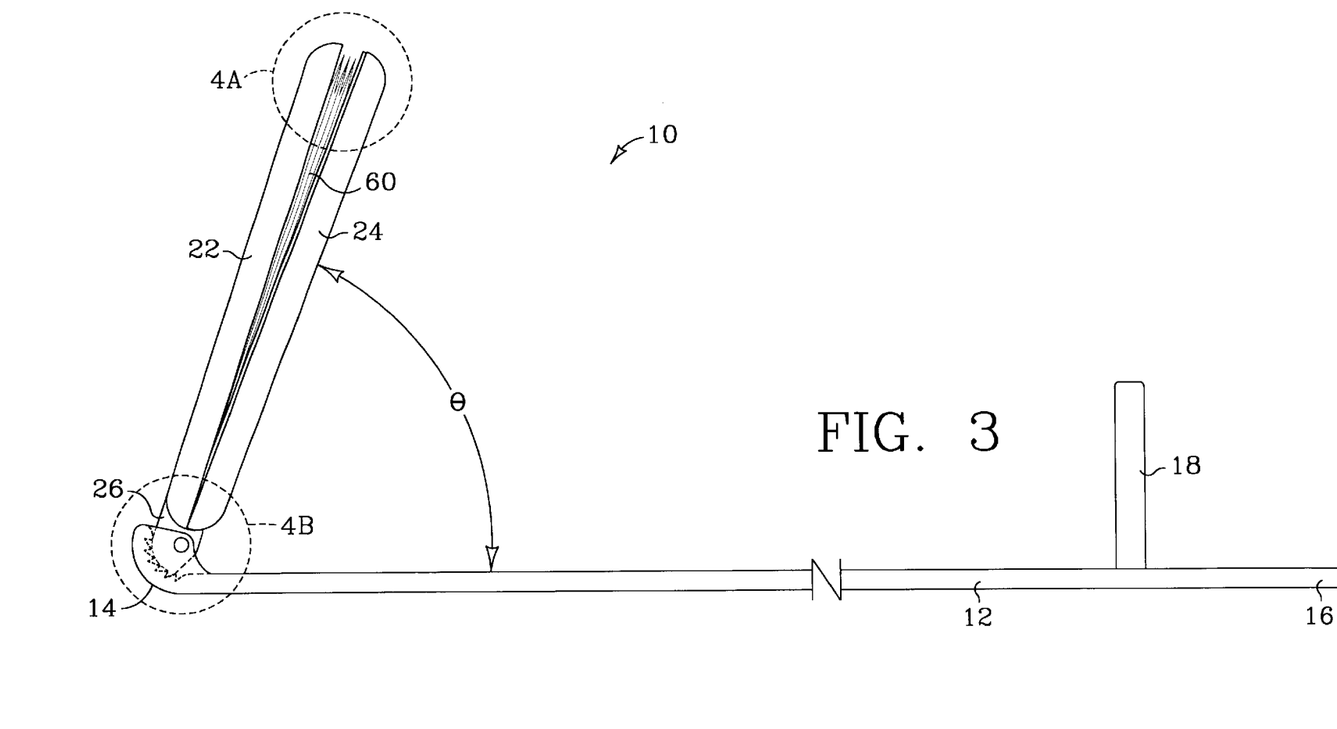
FIG. 3 is a side elevation view of the embodiment of the present invention shown in FIG. 1 depicting the speculum ring in a raised, partially open position.
Figure 4A:
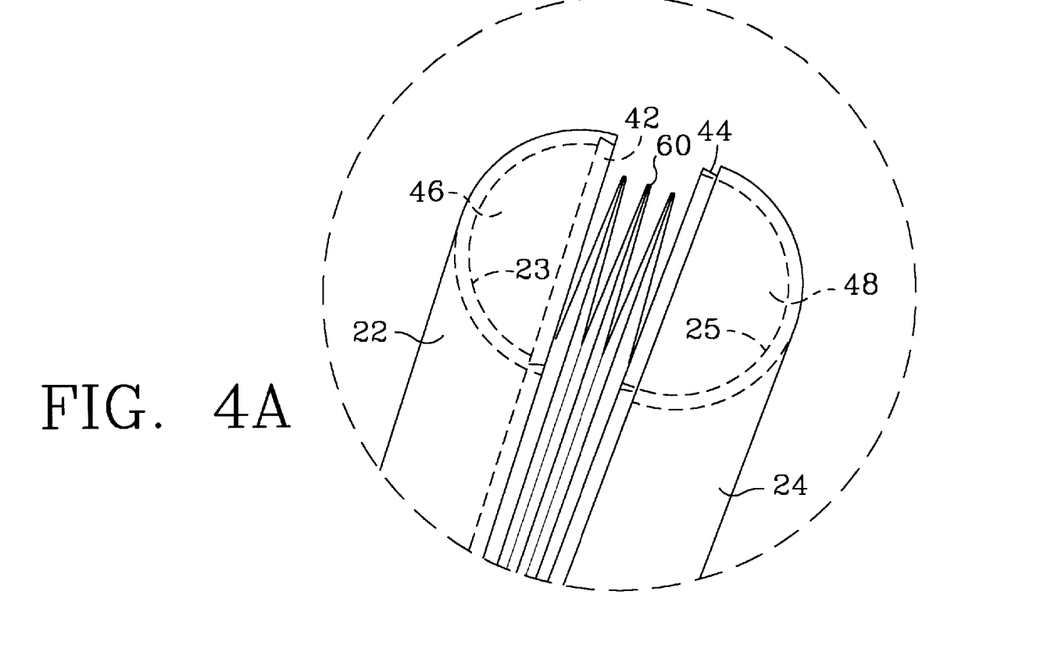
FIG. 4A is a detailed sectional view of the upper portion of the speculum ring of the present invention as shown in FIG. 3.

In a preferred embodiment, speculum ring assembly 20 is a hollow ring, split circumferentially into two halves 22, 24 which house a collapsed flexible tube 60. Referring to FIG. 4A, ring halves 22, 24 include concave surfaces 23, 25 which define interior bores 46, 48. In one embodiment, the adjacent perimeters 42, 44 of each ring half are mating surfaces which help secure the ring halves together. Tube 60 is preferably secured to the interior surfaces 23, 25 of the speculum ring 60. When speculum ring 20 is in the closed position, flexible tube 60 is collapsed or compressed within interior bores 46, 48.

Figure 6:
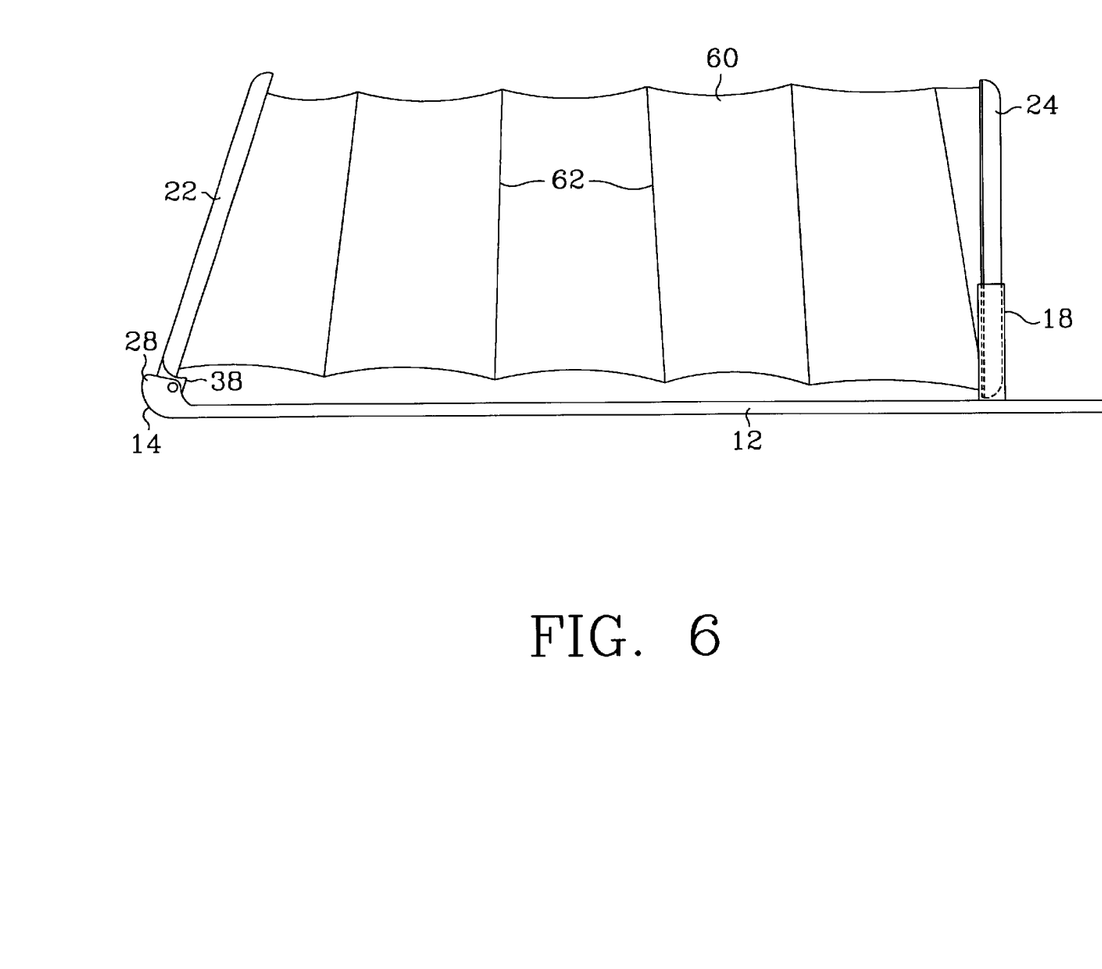
FIG. 6 is a side elevation view of the embodiment of the present invention shown in FIG. 1 in a raised, expanded position.
Figure 7:
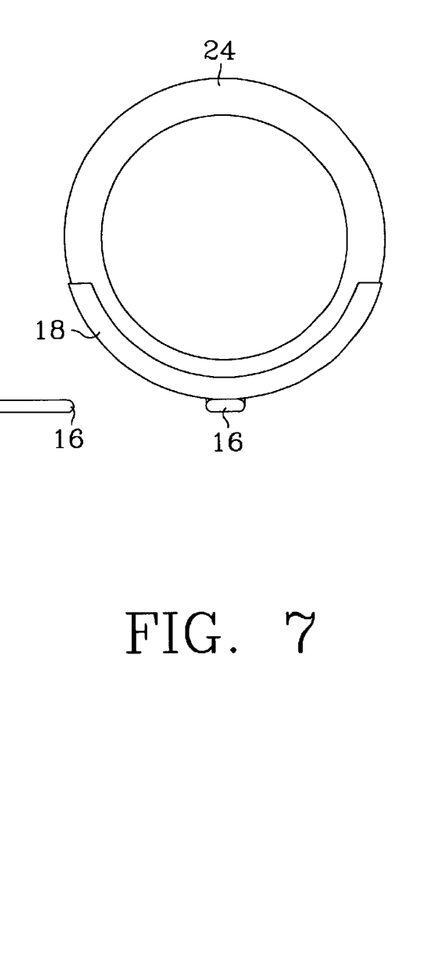
FIG. 7 is a right end elevation view of the embodiment of the present invention shown in FIG. 6.
Figure 8:
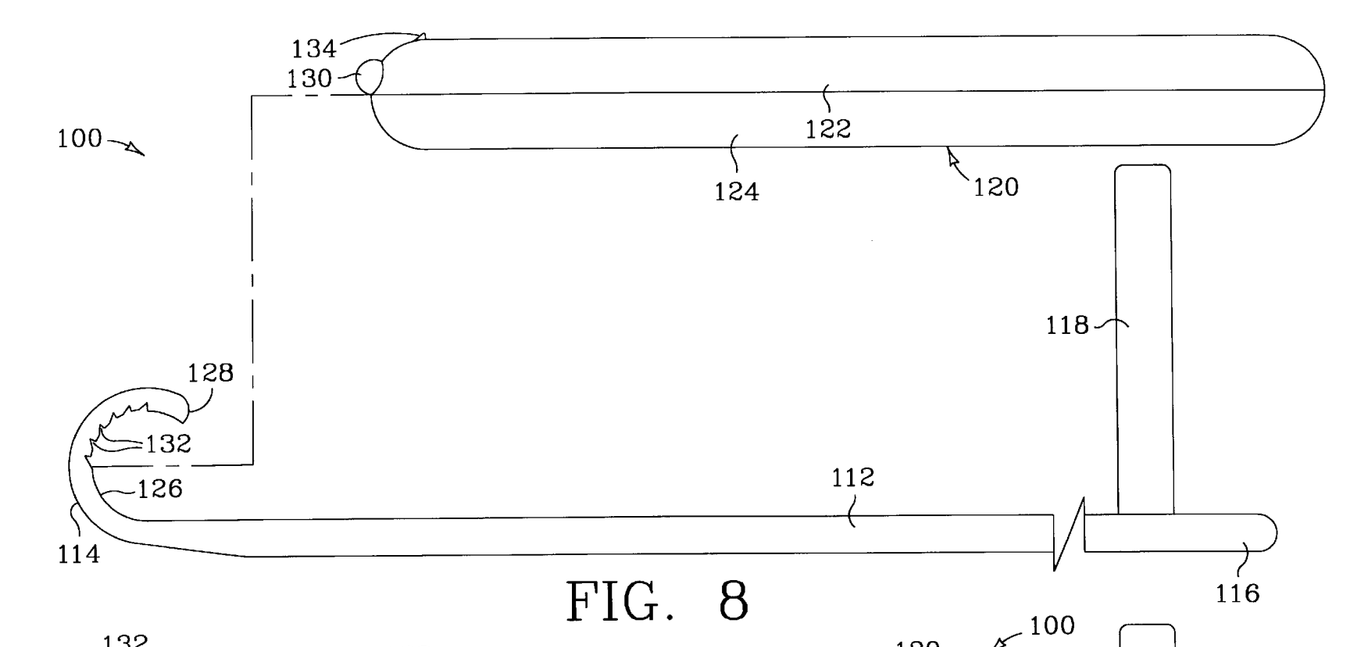
FIG. 8 is a side elevation view of an alternative embodiment of the present invention depicting a detached, compressed speculum ring.
Figure 9:
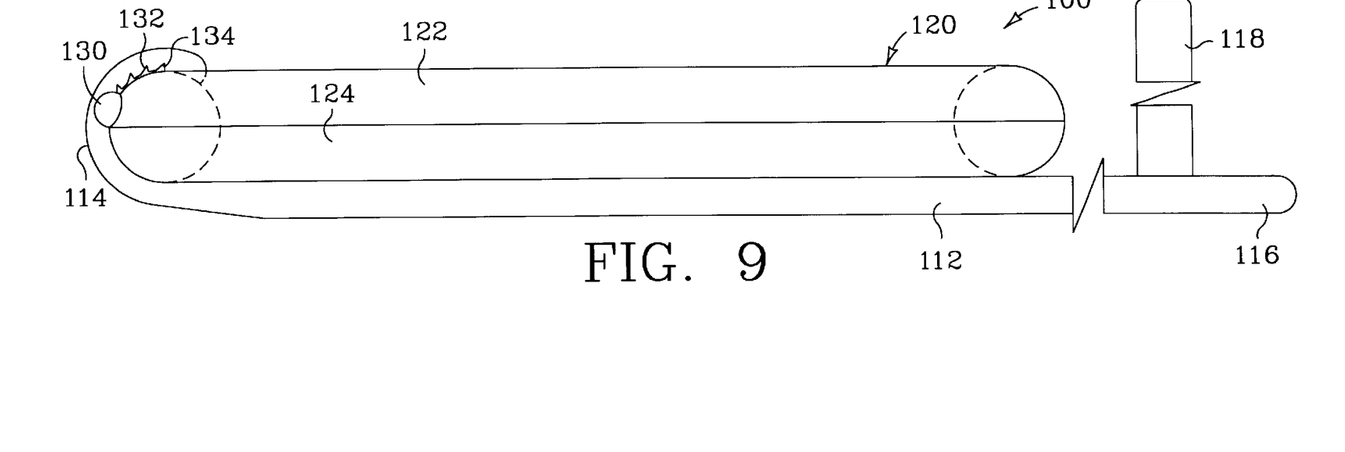
FIG. 9 is a side elevation view of the embodiment of the present invention shown in FIG. 8 depicting the speculum ring in the horizontal, compressed position.
Figures 10, 11:
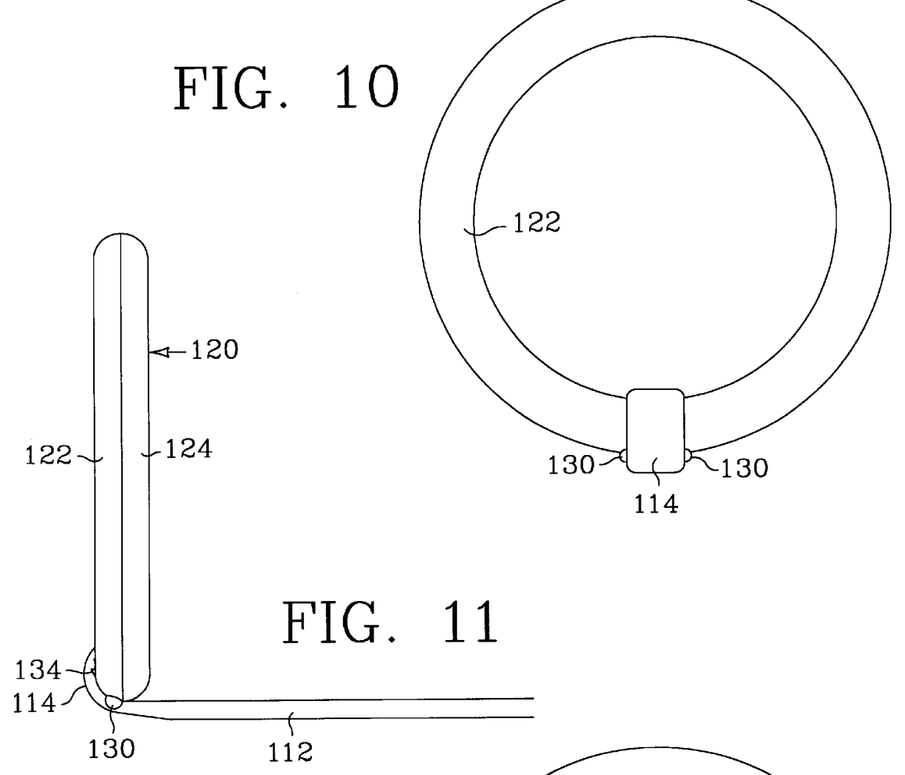
FIG. 10 is a left end elevation view of the embodiment of the present invention shown in FIG. 8.
FIG. 11 is a side elevation view of the embodiment of the present invention shown in FIG. 8 depicting the speculum ring in the raised, compressed position.
Figure 12:
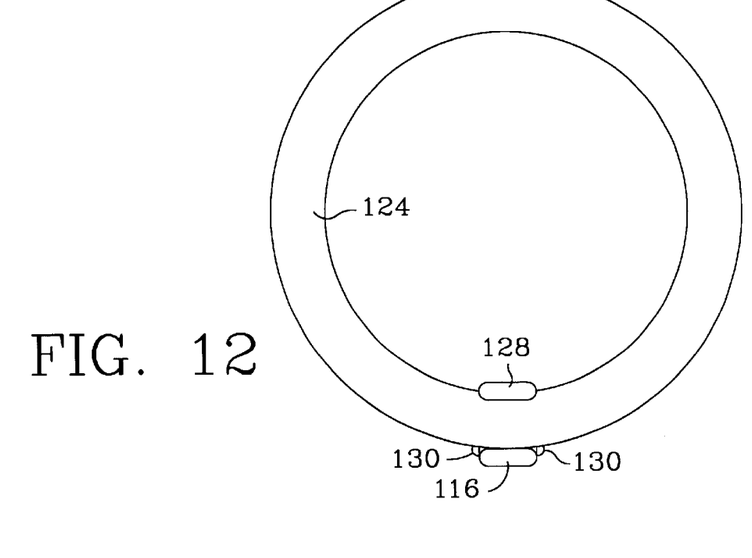
FIG. 12 is a right end elevation view of the embodiment of the present invention shown in FIG. 8.
Figure 13:
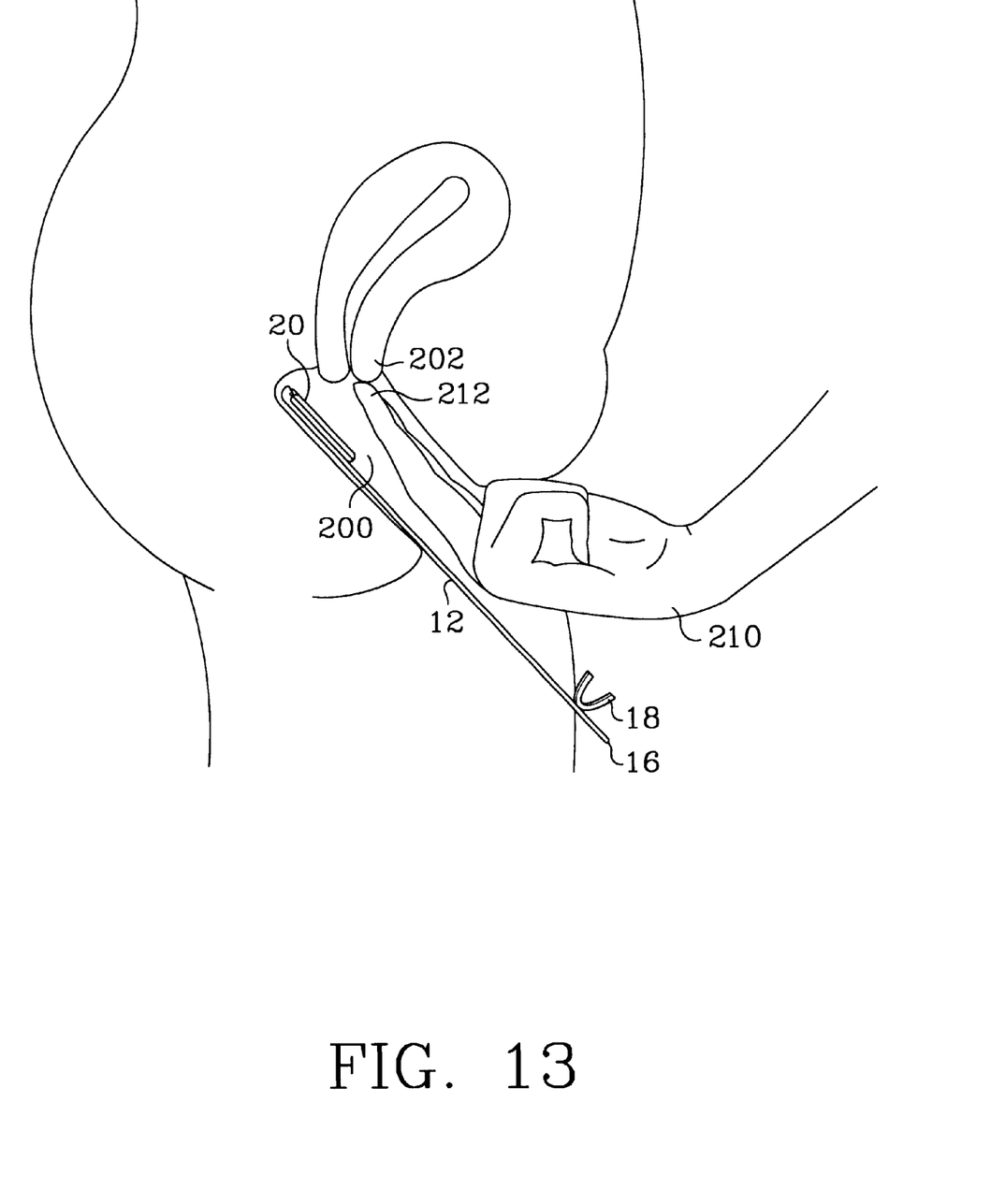
FIG. 13 is a side view of an embodiment of the present invention shown inserted in the user's vagina having the speculum ring in the horizontal, collapsed position, with the user digitally locating the cervix.
Figure 14:
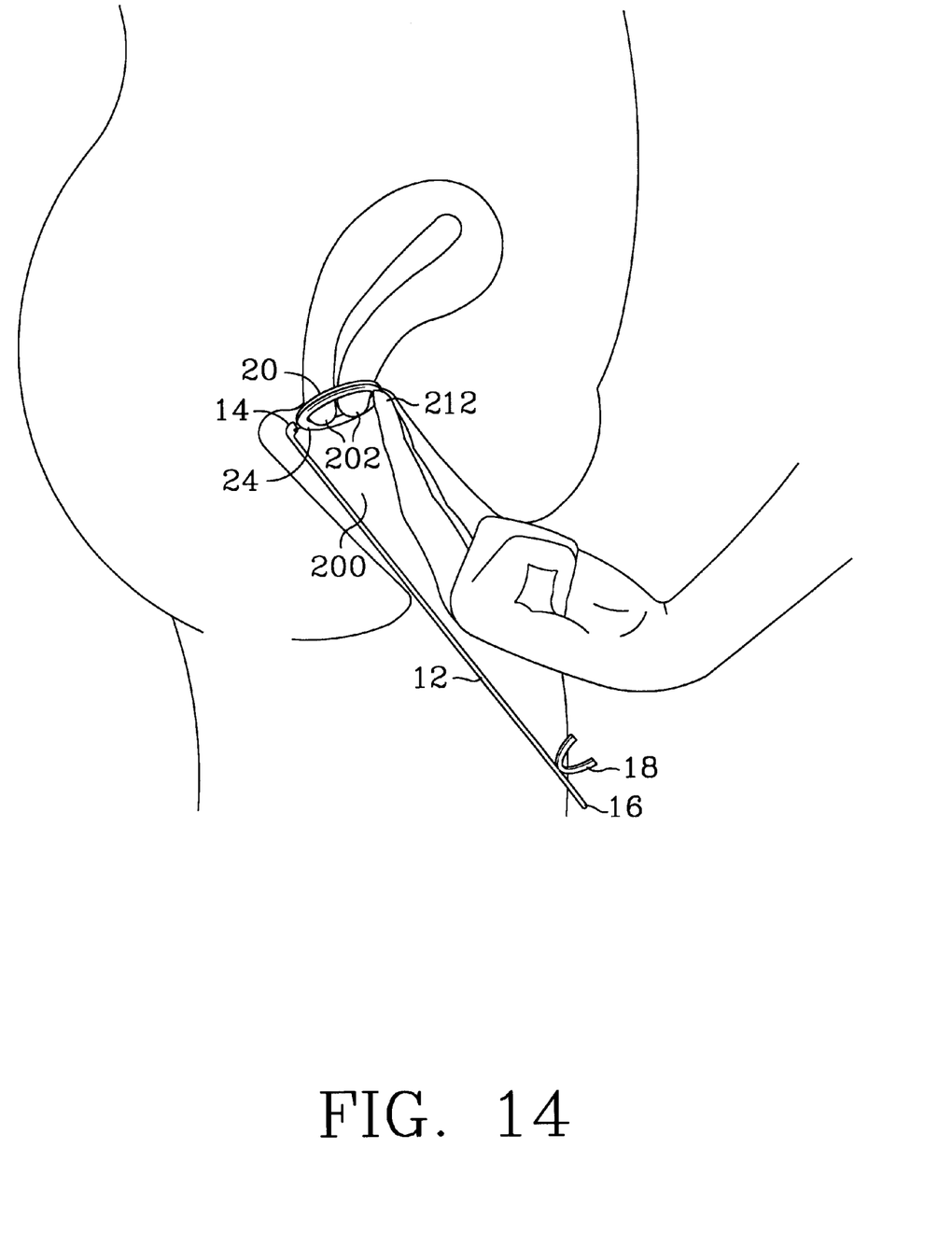
FIG. 14 is a side view of the embodiment of the present invention shown in FIG. 13, with the closed speculum ring digitally raised into position around the user's cervix.
Figure 15:
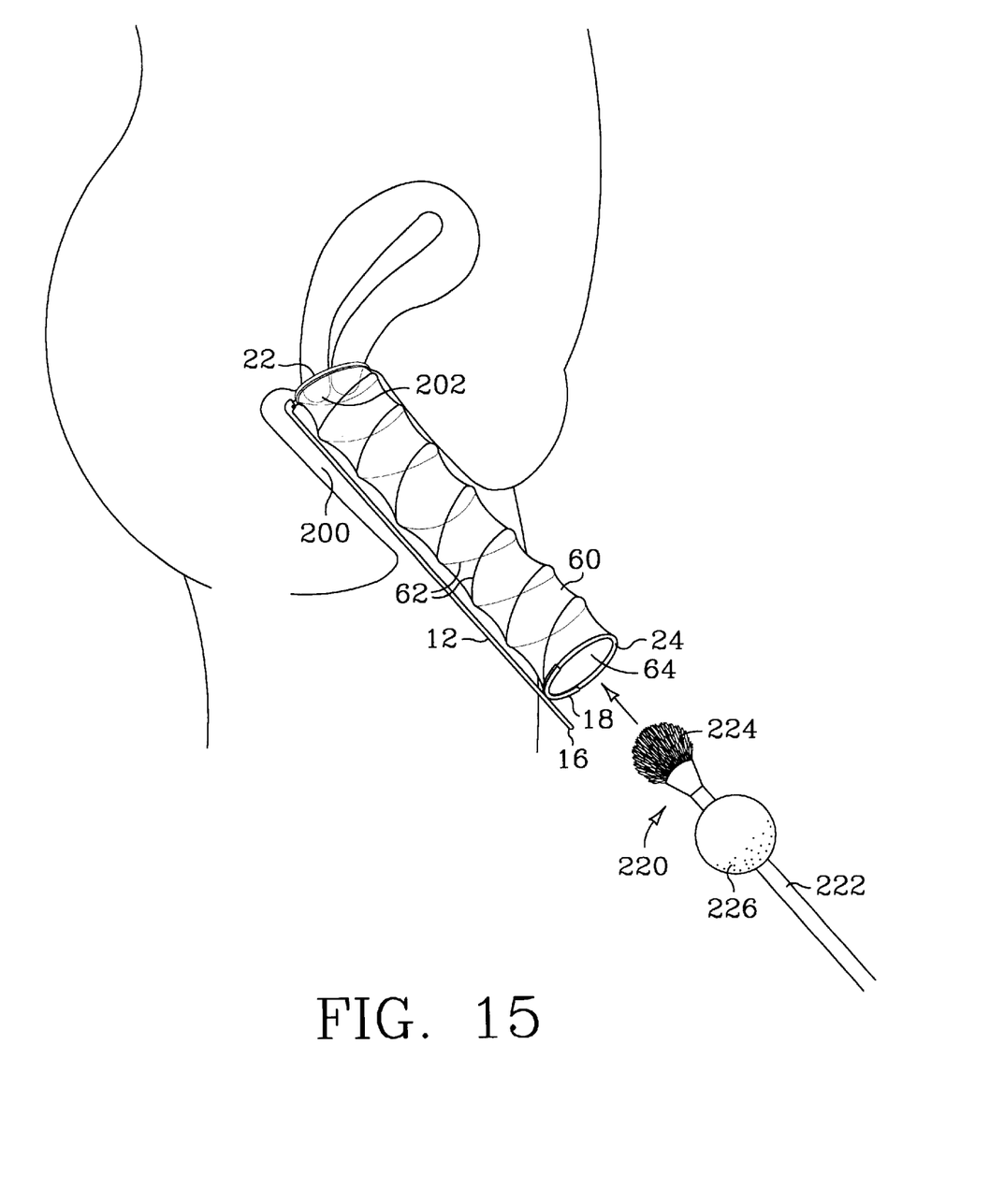
FIG. 15 is a side view of the embodiment of the present invention shown in FIG. 13 with the open speculum ring expanded and a sampling tool positioned for use.

Referring briefly to FIGS. 6 and 15, tube 60 includes a reinforcement means such as a flexible wire 62 which spirals circumferentially through the length of the tube 60. The reinforcement means 62 prevents the tube 60 from collapsing, closing or decreasing the size of bore 64 during use from the pressure exerted by the user's vaginal wall. It will be understood and appreciated by those skilled in the art that the tube may be constructed of any suitable pliable material such as latex, rubber, or plastics.

Figure 4B:
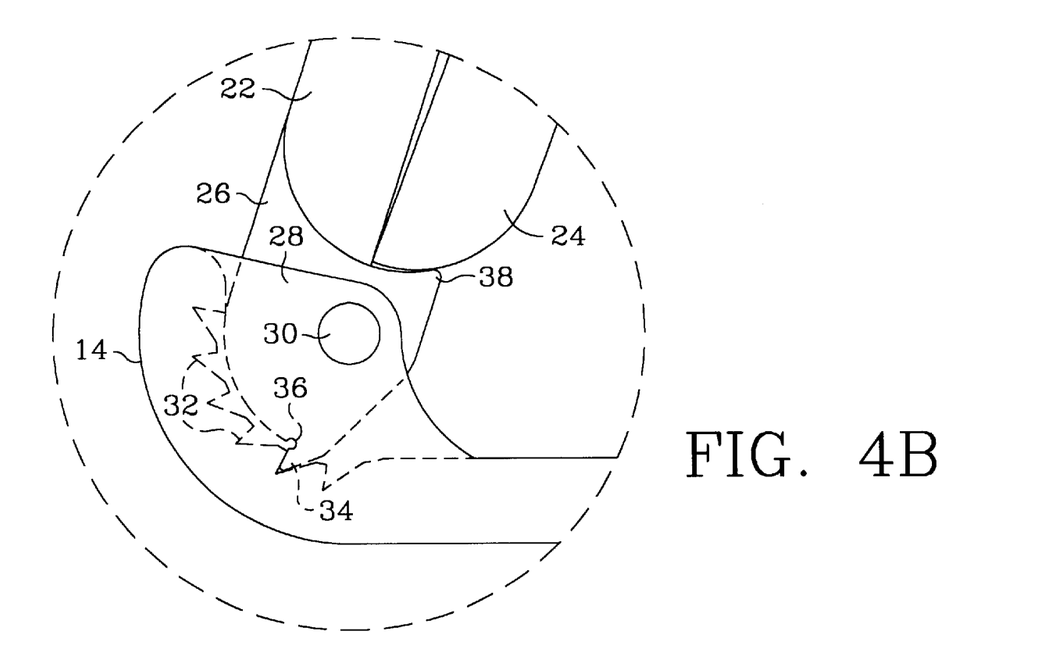
FIG. 4B is a detailed sectional view of the lower portion of the speculum ring of the present invention as shown in FIG. 3.

Referring back to FIGS. 1–4, apparatus 10 includes a means for movably attaching the flexible speculum 20 proximal to first end 14. In one preferred embodiment, the movable attachment means is a ratchet wheel or spur 28 proximal to end 14. With reference to FIG. 4B, ratchet wheel 28 includes a plurality of notches 32 for engaging hinge tab 34 of pawl 26. As shown in FIG. 4B, spindle 30 enables tab 34 of pawl 26 to pivot through notches 32 of wheel 28 when speculum ring 20 is raised from its horizontal position through angle θ. Notch 36 adds flexibility to hinge tab 34 to facilitate motion of the ratchet.

An alternative embodiment of the movable attachment mechanism is shown in FIGS. 8–12. This embodiment includes speculum ring 120 having halves 122, 124, insertion handle 112 having ends 114, 116 and ring holder 118. The alternative movable attachment mechanism includes ratchet wheel 126 having a plurality of notches 132 for engaging hook 134 on first ring half 122. As shown in detail in FIGS. 10–12, guides 130 are provided on both sides of ring half 122 to stabilize and secure speculum ring 120 during the arced movement of ring 120 into position around the user's cervix.

It will be understood and appreciated by one skilled in the art that there are other ratchet and non-ratchet moveable hinge and hook mechanisms known in the art which may be suitable for use with the present invention. Specifically, other mechanisms known in the art may be modified or adapted to permit moveable mounting of the speculum ring 20 to the insertion handle 12 for selective positioning of the speculum ring 20 around the user's cervix.

During use of the invention, ring halves 22, 24 must remain adjacent to each other to contain collapsed tube 60 within bores 46, 48 until the speculum ring 20 is raised into position around the user's cervix. In one embodiment, as shown in FIGS. 1–3 and 4B, pawl 26 includes an extended tab or latch 38 which secures ring half 24 to ring half 22 while ring 20 is moved from its closed, horizontal position to its raised position. Once the ring is placed around the cervix, the user simply gently shifts or lifts ring half 24 away from hook 38 to separate ring half 24 from ring half 22 and expand speculum tube 60.

Figure 5A:
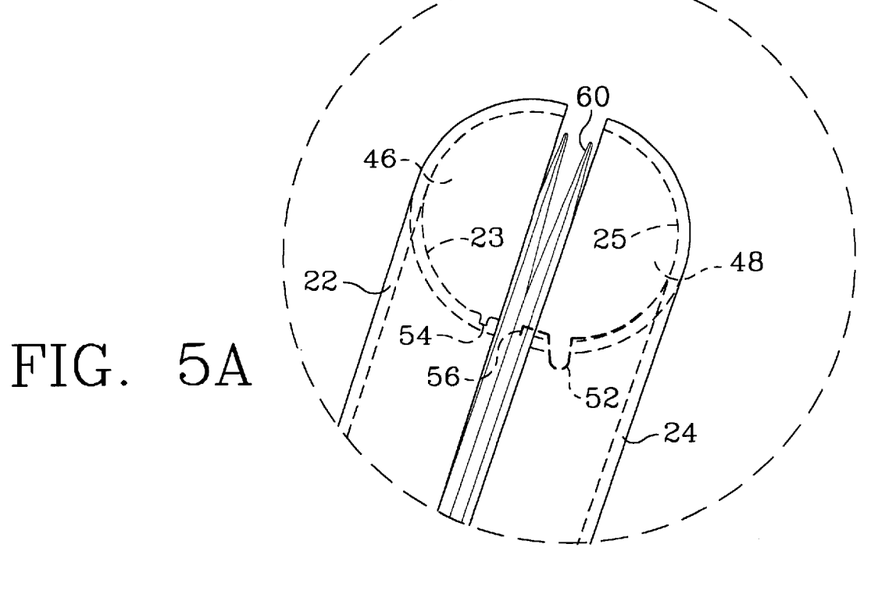
FIG. 5A is a detailed sectional view of an alternative embodiment of the present invention depicting a latching mechanism proximal to the upper portion of the speculum ring.
Figure 5B:
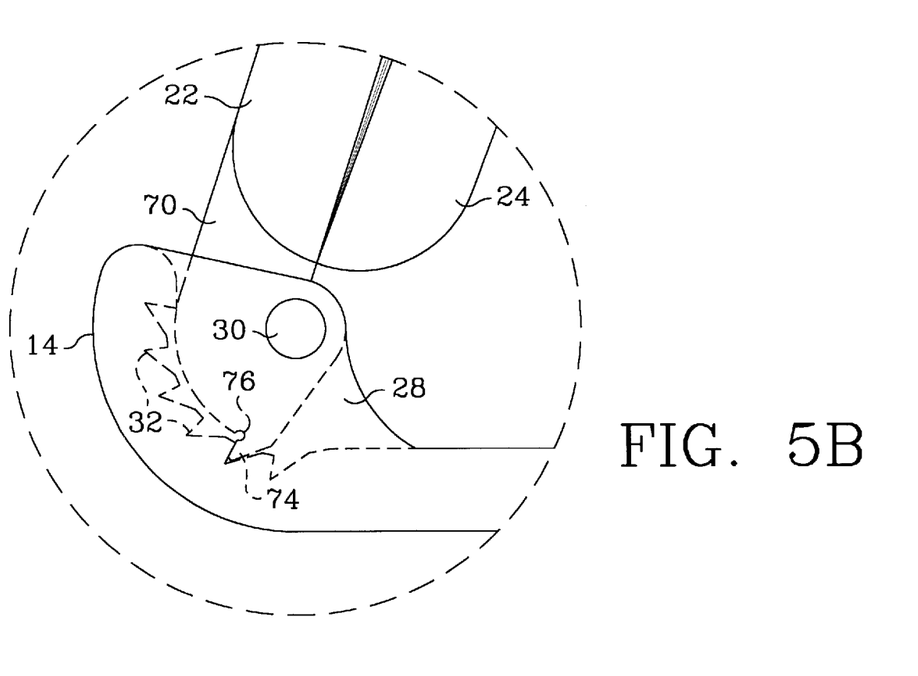
FIG. 5B is a detailed sectional view of an alternative embodiment of the lower portion of the speculum ring of the present invention.

In an alternative embodiment, as shown in FIGS. 5A and 5B, a spring latch is provided having a spring end 56 which when engaged in notch 54 holds the halves 22, 24 adjacent to each other. Once the user is ready to open ring 20 and expand tube 60, button 52 is pushed to separate latch hook 56 from notch 54. Referring to FIG. 5B, in this embodiment, pawl 70 having hinge tab 74 and flex notch 76, does not have a latch for securing halves 22, 24.

It will be understood and appreciated by those skilled in the art that other latching mechanisms and means known in the art may be modified or adapted to prevent premature separation of the speculum ring halves until the user is ready to release and expand tube 60. Such alternatives may include the use of alternative mating surfaces, dovetailed lips, rabbeted joints or interference fits.

As shown in FIGS. 8–12, the latching function is achieved by extended wheel end 128 which wraps a sufficient length around ring half 122 of speculum ring 120, to secure ring half 124 against handle 112 and ring half 122 until insertion is completed and speculum ring 120 is rotated into position around the cervix.

The use and operation of the present invention will be best understood in conjunction with the method of the invention. In the method, the user may chose any comfortable position for personally digitally locating their cervix and handling the speculum and sampling tools. Successful positions include standing with both feet on the floor, standing with one foot resting on a raised surface, reclining, or laying on a bed.

Referring to FIGS. 13–16, the user inserts the flexible speculum 10 with speculum ring 20 in the horizontal, closed position, through the introitus of the user's vagina 200 until end 14 rests below the user's cervix 202. Proper positioning is confirmed by digital 212 location of the cervix 202 by the user. Next, the user raises speculum ring 20 until it encircles the cervix 202. Ring halves 22, 24 are next separated and free half 24 is drawn out through the introitus, expanding tube 60 and defining bore 64, thereby establishing a direct path to the user's cervix 202. Ring half 24 may then be inserted into holder 18 located at the distal end 18 of handle 12.

It should be understood by those skilled in the art that aids to help the user withdraw the free ring half through the vagina to extend the tube may readily be adapted for the speculum tool. For example, a finger grip, string or other tether device may be added to the free ring half to facilitate the user's movement of the free ring half back out of the introitus and into holder 18.

Figure 16:
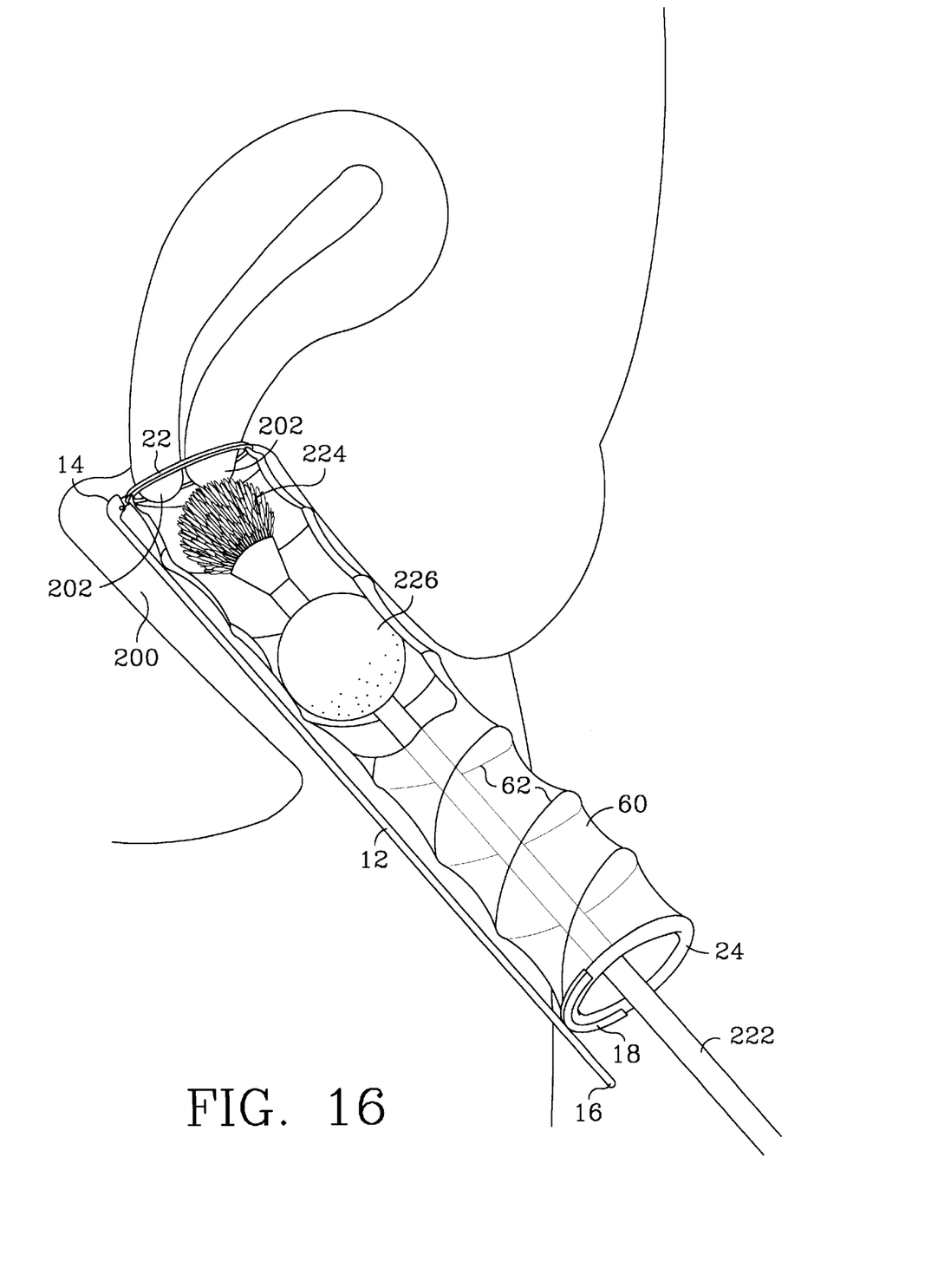
FIG. 16 is a partial cut-away side view of the embodiment of the present invention shown in FIG. 13 with the sampling tool in use within the bore of the expanded speculum ring.

In the next step, a sampling tool 220 is directed into bore 64 of tube 60 and advanced to the cervix 202 where rotating the brush 224 gently against the cervix 202 assures collection of an adequate sample. Preferably, tool 220 includes a brush centering guide such as sphere 226 located on handle 222 proximal to the brush end 224. Centering guide 226 helps keep the brush 220 centered as it traverses bore 64 to ensure appropriate contact of brush 224 with the cervix 202. The guide 226 will also decrease the likelihood of losing sampled tissue against the interior surface of tube 60 when withdrawing the tool from bore 64.

The sampling tool is next withdrawn from the vagina and preserved for tissue collection and analysis. Additional or alternative sampling tools known in the art for collection of tissue samples in the endocervical canal and surrounding surface area may be used. Upon completion of the sampling process, the speculum apparatus 10 is next withdrawn and discarded. The tissue samples may be handled in any number of conventional ways known in the art. For example, the brush of the sampling tool may be sealed in a fixative and sent to a lab, gynecologist or pathologist for interpretation of the samples.

It will be understood and appreciated by those skilled in the art that the apparatus of the present invention is readily adaptable for use in conjunction with multiple tools for vaginal cell, tissue and mucus sampling. It will be further understood and appreciated by those skilled in the art that the present invention may be changed or modified using alternative mechanisms and materials known in the art without departing from the spirit and scope of the invention as defined in the following claims.

What is claimed is:

1. An apparatus for obtaining a PAP smear from a woman's cervix, comprising:
    a flexible speculum including a hollow ring having adjacent first and second halves;
    an insertion handle having a first end, a second end, and a means for movably attaching the flexible speculum adjacent to said first end; and
    a flexible tube compressed within said hollow ring, having a first tube end attached to the first half of the ring, a second tube end attached to the second half of the ring, a bore, a length and a circumference; wherein said flexible tube is expanded by separating the first and second adjacent ring halves and moving the second ring half proximal to the second end of the insertion handle.

2. The PAP smear apparatus of claim 1, further comprising a tissue sampling tool having a handle, a collection end and a spherical centering guide.

3. The PAP smear apparatus of claim 1, wherein the second ring half of the flexible speculum is secured proximal to the second end of the insertion handle when the flexible tube is expanded.

4. The PAP smear apparatus of claim 1, wherein the means for movably attaching the flexible speculum adjacent to the first end of the insertion handle is a hinge.

5. The PAP smear apparatus of claim 1, wherein the means for movably attaching the flexible speculum adjacent to the first end of the insertion handle is a ratchet mechanism.

6. The PAP smear apparatus of claim 5, wherein the ratchet mechanism includes a pawl on the first ring half and a spur proximal to the first end of the insertion handle.

7. The PAP smear apparatus of claim 4, wherein the ratchet mechanism includes a catch on the first ring half and a plurality of teeth proximal to the first end of the insertion handle.

8. The PAP smear apparatus of claim 1, further comprising a mechanism for securing the first and second ring halves together until the flexible tube is expanded.

9. The PAP smear apparatus of claim 8, wherein the first and second halves include adjacent mating surfaces.

10. The PAP smear apparatus of claim 8, wherein the first and second ring halves include a latching mechanism.

11. The PAP smear device of claim 1 0, wherein the latching mechanism is a spring latch.

12. The PAP smear device of claim 10, wherein the latching mechanism is a hook.

13. The PAP smear apparatus of claim 1, wherein the tube includes a reinforcement means to prevent the tube from collapsing after expansion.

14. The PAP smear apparatus of claim 13, wherein the reinforcement means is a flexible wire coiled circumferentially through the length of the tube.

15. The PAP smear apparatus of claim 1, further comprising a means for separating the adjacent ring halves and drawing the second ring half out of the user's vagina.

16. The PAP smear apparatus of claim 15, wherein the means for separating the adjacent first and second ring halves is a string attached to the second ring half.

17. A method for obtaining a PAP smear from the cervix of a woman comprising the steps of:
    inserting a flexible speculum through the introitus of the user's vagina, said flexible speculum including an insertion handle, a hollow ring having first and second halves, a collapsed tube having a length and circumference housed within the ring, and a means for movably attaching the ring to the insertion handle;
    positioning the ring so that it encircles the user's cervix;
    separating the first and second ring halves; and
    expanding the collapsed tube by drawing the second half of the ring back out the user's vagina.

18. The method of claim 17, further comprising the step of securing the second ring half to the distal end of the insertion handle.

19. The method of claim 17, further comprising the steps of:
    inserting a sampling tool through the bore of the tube;
    wiping the cervix with the sampling tool to collect a tissue sample;
    removing the sampling tool from the tube; and
    removing the flexible speculum from the user's vagina.

20. The method of claim 19, further comprising the step of sealing the sampling tool in a fixative for later analysis of the collected tissue sample.

* * * * *